US011266338B1

(12) United States Patent
Tao et al.

(10) Patent No.: US 11,266,338 B1
(45) Date of Patent: Mar. 8, 2022

(54) AUTOMATIC DEPRESSION DETECTION METHOD AND DEVICE, AND EQUIPMENT

(71) Applicant: Institute of Automation, Chinese Academy of Sciences, Beijing (CN)

(72) Inventors: Jianhua Tao, Beijing (CN); Mingyue Niu, Beijing (CN); Bin Liu, Beijing (CN); Qifei Li, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/389,381

(22) Filed: Jul. 30, 2021

(30) Foreign Application Priority Data

Jan. 4, 2021 (CN) .......................... 202110001070.9

(51) Int. Cl.
*A61B 5/16* (2006.01)
*A61B 5/00* (2006.01)
*G06N 20/10* (2019.01)

(52) U.S. Cl.
CPC ............ *A61B 5/165* (2013.01); *A61B 5/7257* (2013.01); *A61B 5/7267* (2013.01); *G06N 20/10* (2019.01); *A61B 2560/02* (2013.01)

(58) Field of Classification Search
CPC ..... A61B 5/165; A61B 5/7257; A61B 5/7267; A61B 2560/02; G06N 20/10
See application file for complete search history.

(56) References Cited

U.S. PATENT DOCUMENTS

| 7,870,574 | B2 * | 1/2011 | Kenyon | G10L 25/48 725/19 |
| 9,355,635 | B2 * | 5/2016 | Gao | G06K 9/00744 |
| 10,812,424 | B1 * | 10/2020 | Bommaraju | G06N 5/003 |
| 11,144,764 | B1 * | 10/2021 | Sharma | H04N 21/233 |

(Continued)

FOREIGN PATENT DOCUMENTS

| CN | 101930619 A | 12/2010 |
| CN | 107133481 A | 9/2017 |

(Continued)

*Primary Examiner* — Christopher A Flory
(74) *Attorney, Agent, or Firm* — Bayramoglu Law Offices LLC

(57) ABSTRACT

An automatic depression detection method includes the following steps of: inputting audio and video files, wherein the audio and video files contain original data in both audio and video modes; conducting segmentation and feature extraction on the audio and video files to obtain a plurality of audio segment horizontal features and video segment horizontal features; combining segment horizontal features into an audio horizontal feature and a video horizontal feature respectively by utilizing a feature evolution pooling objective function; and conducting attentional computation on the segment horizontal features to obtain a video attention audio feature and an audio attention video feature, splicing the audio horizontal feature, the video horizontal feature, the video attention audio feature and the audio attention video feature to form a multimodal spatio-temporal representation, and inputting the multimodal spatio-temporal representation into support vector regression to predict the depression level of individuals in the input audio and video files.

9 Claims, 2 Drawing Sheets

(56) References Cited

U.S. PATENT DOCUMENTS

| | | | | |
|---|---|---|---|---|
| 11,176,444 B2* | 11/2021 | Wall | | G06N 3/08 |
| 2003/0112265 A1* | 6/2003 | Zhang | | G06F 16/745 |
| | | | | 715/723 |
| 2012/0123780 A1* | 5/2012 | Gao | | H04N 21/44029 |
| | | | | 704/245 |
| 2014/0052465 A1* | 2/2014 | Madan | | G16H 40/60 |
| | | | | 705/2 |
| 2016/0006944 A1* | 1/2016 | Voss | | G11B 27/28 |
| | | | | 348/571 |
| 2016/0111130 A1* | 4/2016 | Lu | | G11B 27/034 |
| | | | | 386/278 |
| 2017/0258390 A1* | 9/2017 | Howard | | A61B 5/16 |
| 2018/0039745 A1* | 2/2018 | Chevalier | | G16H 30/20 |
| 2018/0103903 A1* | 4/2018 | Tzvieli | | G02B 27/0172 |
| 2018/0104439 A1* | 4/2018 | Tzvieli | | A61B 5/0816 |
| 2018/0144746 A1* | 5/2018 | Mishra | | G10L 15/25 |
| 2019/0043618 A1* | 2/2019 | Vaughan | | G16H 50/20 |
| 2019/0043619 A1* | 2/2019 | Vaughan | | G16H 20/10 |
| 2019/0110754 A1* | 4/2019 | Rao | | G16H 50/20 |
| 2019/0172462 A1* | 6/2019 | Mishra | | G10L 25/51 |
| 2019/0189259 A1* | 6/2019 | Clark | | G16H 70/40 |
| 2019/0384392 A1* | 12/2019 | Aimone | | G06F 3/015 |
| 2020/0037942 A1* | 2/2020 | Howard | | A61B 5/4088 |
| 2020/0121236 A1* | 4/2020 | Gao | | A61B 5/165 |
| 2021/0133509 A1* | 5/2021 | Wall | | G06N 20/00 |
| 2021/0165490 A1* | 6/2021 | Aimone | | G06F 3/0487 |
| 2021/0169417 A1* | 6/2021 | Burton | | A61B 5/02055 |
| 2021/0183516 A1* | 6/2021 | Chevalier | | G16H 10/60 |
| 2021/0201004 A1* | 7/2021 | Yadav | | G10L 25/21 |
| 2021/0259557 A1* | 8/2021 | Frank | | A61B 5/015 |
| 2021/0275034 A1* | 9/2021 | Frank | | A61B 5/015 |
| 2021/0319897 A1* | 10/2021 | Howard | | G16H 40/20 |

FOREIGN PATENT DOCUMENTS

| | | |
|---|---|---|
| CN | 108200483 A | 6/2018 |
| CN | 109431521 A | 3/2019 |
| CN | 110188343 A | 8/2019 |
| CN | 111723239 A | 9/2020 |
| WO | 2020196976 A1 | 1/2020 |

* cited by examiner

AUTOMATIC DEPRESSION DETECTION METHOD AND DEVICE, AND EQUIPMENT

CROSS REFERENCE TO THE RELATED APPLICATIONS

This application is based upon and claims priority to Chinese Patent Application No. 202110001070.9 filed on Jan. 4, 2021, the entire contents of which are incorporated herein by reference.

TECHNICAL FIELD

The embodiments of the application relate to the technical field of data processing, in particular to an automatic depression detection method and device, and equipment.

BACKGROUND

Depression is a mental disease, which seriously affects people's physical and mental health. At present, doctors for treating mental diseases are extremely scarce, and many patients cannot get early treatment, thus missing the best time window to get the disease controlled. Automatic depression detection is an important research direction in the fields of human-computer interaction and artificial intelligence. The purpose of automatic depression detection is to explore the changes of voice and face from healthy individuals to patients suffering from depression, and to put forward corresponding models and methods to establish the ability of a machine to capture depression clues, enhance its diagnostic ability and improve its diagnostic efficiency. In the prior art, the depression level is mainly predicted by extracting multiple segments of features which can depict individuals from audio and video files of them, combining the multiple segments of features into an overall feature, and then analyzing the feature.

There is a problem in the prior art that the existing feature extraction method is not directed to a depression detection task, so the accuracy of depression detection is not high. Another problem is that during the combination of the multiple segments of features, different segments of features are simply spliced, the information in each segment of feature cannot be completely contained, and the interactive relationship among various features is not considered, so the accuracy of the depression detection task is not high.

SUMMARY

The embodiments of the application provide an automatic depression detection method and device, and equipment, aiming at improving the accuracy of depression detection.

A first aspect of the embodiments of the application provides an automatic depression detection method, the method comprises:

inputting audio and video files, wherein the audio and video files contain original data of two modes comprising a long-time audio file and a long-time video file;

extracting a Fourier amplitude spectrum of the long-time audio file, dividing the Fourier amplitude spectrum into a plurality of spectral segments with a fixed size, and dividing the long-time video file into a plurality of video segments with a fixed frame number;

inputting each spectral segment and video segment into an audio spatio-temporal attention network and a video spatio-temporal attention network respectively to obtain a plurality of audio segment horizontal features and a plurality of video segment horizontal features;

constructing a feature evolution pooling objective function for the plurality of audio segment horizontal features and the plurality of video segment horizontal features, and conducting optimization solution to obtain a result matrix;

combining the plurality of audio segment horizontal features and video segment horizontal features into an audio horizontal feature and a video horizontal feature respectively by using the result matrix;

extracting a video attention audio feature and an audio attention video feature according to the plurality of audio horizontal features and video horizontal features respectively;

splicing the audio horizontal feature, the video horizontal feature, the video attention audio feature and the audio attention video feature to form a multimodal spatio-temporal representation; and inputting the multimodal spatio-temporal representation into support vector regression to predict the depression level of individuals in the input audio and video files.

Optionally, extracting a Fourier amplitude spectrum of the long-time audio file, dividing the Fourier amplitude spectrum into a plurality of spectral segments with a fixed size, and dividing the long-time video file into a plurality of video segments with a fixed frame number comprise:

extracting a voice file from the long-time audio file with an original format of MP4, and saving the voice file in a way format to obtain a way file;

processing the way file by means of fast Fourier transform to obtain a Fourier spectrum;

conducting amplitude calculation on the Fourier spectrum to obtain a Fourier amplitude spectrum;

dividing the Fourier amplitude spectrum by taking a first preset frame number as a window length and a second preset frame number as a frame shift to obtain the plurality of amplitude spectrum segments, wherein the label of the plurality of amplitude spectrum segments is the label corresponding to the way file;

saving the amplitude spectrum segments in a mat format;

extracting all video frames in the long-time video file and normalizing all the video frames to a preset size to obtain a video frame sequence; and dividing the video frame sequence by taking a third preset frame number as a window length and a fourth preset frame number as a frame shift to obtain video segments, wherein the label of the video segments is the label corresponding to the long-time video file.

Optionally, inputting the plurality of spectral segments and the plurality of video segments into spatio-temporal attention networks to obtain a plurality of audio segment horizontal features and video segment horizontal features comprises:

inputting the marked spectral segments and video segments into the audio spatio-temporal attention network and the video spatio-temporal attention network respectively as training sets in advance for training, so as to obtain a trained audio spatio-temporal attention network and a trained video spatio-temporal attention network; and inputting the plurality of spectral segments and the plurality of video segments into the trained audio spatio-temporal attention network and the trained video spatio-temporal attention network respectively to obtain the plurality of audio segment horizontal features and the plurality of video segment horizontal features.

Optionally, the feature evolution pooling objective function is as follows:

$$G^* = \mathrm{argmin}_{G^T G = I_k} \Sigma_{i=1}^D \|GG^T d_i^T - d_i^T\|^2$$

where G is a known matrix, $G^T$ is a transposed matrix of the matrix G, $d_i^T$ is a transposition of an <I>th video segment horizontal feature or audio segment horizontal feature, D is the number of the audio segment horizontal features or the video segment horizontal features, $I_k$ indicates that the matrix G is a K-order matrix, G* is the result matrix, and argmin( ) indicates the value of an eigenvector when the formula in the brackets reaches a minimum value.

Optionally, combining the plurality of audio segment horizontal features and video segment horizontal features into an audio horizontal feature and a video horizontal feature respectively by using the optimization result of feature combining evolution comprises:

arranging the plurality of audio segment horizontal features and the plurality of video segment horizontal features into an audio matrix and a video matrix respectively in sequence; and multiplying the audio matrix and the video matrix by a first column of the result matrix respectively to obtain the audio horizontal feature and the video horizontal feature.

Optionally, extracting a video attention audio feature and an audio attention video feature according to the plurality of audio horizontal features and video horizontal features respectively comprises:

calculating the plurality of audio segment horizontal features by using an attention mechanism to obtain the video attention audio feature; and calculating the plurality of video segment horizontal features by using the attention mechanism to obtain the audio attention video feature.

Optionally, when calculating the plurality of audio segments by using an attention mechanism to obtain the video attention audio feature, the calculation method is as follows:

$$\mathrm{VAAF} = [S_1^A, \ldots, S_{M_A}^A]\alpha$$

wherein VAAF is the video attention audio feature, $S_j^A$ (j=1, . . . , $M_A$) is the feature of a <j>th audio segment, $\alpha$ is a video attention weight, and the calculation formula of each element in $\alpha = [\alpha_1, \ldots, \alpha_{M_A}]^T$ is as follows:

$$\alpha_j = \frac{e^{(L_V, s_j^A)}}{\sum_{k=1}^{M_A} e^{(L_V, s_k^A)}}, j = 1, \ldots, M_A$$

where $L_V$ is the video horizontal feature, $S_j^A$ (j=1, . . . , $M_A$) is the feature of the <j>th audio segment, and e is a base of a natural logarithm.

Optionally, when calculating the plurality of video segments by using the attention mechanism to obtain the audio attention video feature, the calculation method is as follows:

$$\mathrm{AAVF} = [S_1^V, \ldots, S_{M_V}^V]\beta$$

wherein AAVF is the audio attention video feature, $S_j^V$ (j=1, . . . , $M_V$) is the feature of a <j>th video segment, $\beta$ is an audio attention weight, and the calculation formula of each element in $\beta = [\beta_1, \ldots, \beta_{M_V}]^T$ is as follows:

$$\beta_j = \frac{e^{(L_A, s_j^V)}}{\sum_{k=1}^{M_V} e^{(L_A, s_k^V)}}, j = 1, \ldots, M_V$$

where $L_A$ is the audio horizontal feature, $S_j^V$ (j=1, . . . , $M_V$) is the feature of the <j>th audio segment, and e is a base of a natural logarithm.

A second aspect of the embodiments of the application provides an automatic depression detection device, the device comprises:

an audio and video inputting module for inputting audio and video files, wherein the audio and video files contain original data of two modes, that is, a long-time audio file and a long-time video file;

an audio and video dividing module for extracting a Fourier amplitude spectrum of the long-time audio file, dividing the Fourier amplitude spectrum into a plurality of spectral segments with a fixed size, and dividing the long-time video file into a plurality of video segments with a fixed frame number;

a segment horizontal feature extracting module for inputting each spectral segment and video segment into an audio spatio-temporal attention network and a video spatio-temporal attention network respectively to obtain a plurality of audio segment horizontal features and a plurality of video segment horizontal features;

an optimization solution module for constructing a feature evolution pooling objective function for the plurality of audio segment horizontal features and the plurality of video segment horizontal features, and conducting optimization solution to obtain a result matrix;

a feature combining module for combining the plurality of audio segment horizontal features and video segment horizontal features into an audio horizontal feature and a video horizontal feature respectively by using the result matrix;

an attention feature extracting module for extracting a video attention audio feature and an audio attention video feature according to the plurality of audio horizontal features and video horizontal features respectively;

a multimodal spatio-temporal representation module for splicing the audio horizontal feature, the video horizontal feature, the video attention audio feature and the audio attention video feature to form a multimodal spatio-temporal representation; and a depression level predicting module for inputting the multimodal spatio-temporal representation into support vector regression to predict the depression level of individuals in the input audio and video files.

Optionally, the audio and video dividing module comprises:

a voice file extracting submodule for extracting a voice file from the long-time audio file with an original format of MP4, and saving the voice file in a way format to obtain a way file;

a fast Fourier transform submodule for processing the way file by means of fast Fourier transform to obtain a Fourier spectrum;

an amplitude extracting submodule for conducting amplitude calculation on the Fourier spectrum to obtain a Fourier amplitude spectrum;

an amplitude spectrum dividing submodule for dividing the Fourier amplitude spectrum by taking a first preset frame number as a window length and a second preset frame number as a frame shift to obtain the plurality of amplitude spectrum segments, wherein the label of the plurality of amplitude spectrum segments is the label corresponding to the way file;

an amplitude spectrum segment saving submodule for saving the amplitude spectrum segments in a mat format;

a video frame extracting submodule for extracting all video frames in the long-time video file and normalizing all the video frames to a preset size to obtain a video frame; and a video dividing submodule for dividing the video frame sequence by taking a third preset frame number as a window length and a fourth preset frame number as a frame shift to obtain video segments, wherein the label of the video segments is the label corresponding to the long-time video file.

Optionally, the segment horizontal feature extracting module comprises:

a network training submodule for inputting the marked spectral segments and video segments into the audio spatio-temporal attention network and the video spatio-temporal attention network respectively as training sets in advance for training, so as to obtain a trained audio spatio-temporal attention network and a trained video spatio-temporal attention network; and a segment horizontal feature extracting submodule for inputting the plurality of spectral segments and the plurality of video segments into the trained audio spatio-temporal attention network and the trained video spatio-temporal attention network respectively to obtain the plurality of audio segment horizontal features and the plurality of video segment horizontal features.

Optionally, in constructing a feature evolution pooling objective function for the plurality of audio segment horizontal features and the plurality of video segment horizontal features, and conducting optimization solution to obtain a result matrix, the feature evolution pooling objective function is:

$$G^* = \mathrm{argmin}_{G^T G = I_k} \Sigma_{i=1}^D \|GG^T d_i^T - d_i^T\|^2$$

wherein G is a known matrix, $G^T$ is a transposed matrix of the matrix G, $d_i^T$ is a transposition of an <I>th video segment horizontal feature or audio segment horizontal feature, D is the number of the audio segment horizontal features or the video segment horizontal features, $I_k$ indicates that the matrix G is a K-order matrix, G* is the result matrix, and argmin( ) indicates the value of an eigenvector when the formula in the brackets reaches a minimum value.

Optionally, the feature combining module comprises:

a feature arranging submodule for arranging the plurality of audio segment horizontal features and the plurality of video segment horizontal features into an audio matrix and a video matrix respectively in sequence; and a feature calculation submodule for multiplying the audio matrix and the video matrix by a first column of the result matrix respectively to obtain the audio horizontal feature and the video horizontal feature.

Optionally, the attention feature extracting module comprises:

a first attention feature extracting submodule for calculating the plurality of audio segment horizontal features by using an attention mechanism to obtain the video attention audio feature; and a second attention feature extracting submodule for calculating the plurality of video segment horizontal features by using the attention mechanism to obtain the audio attention video feature.

Optionally, calculating the plurality of audio segment horizontal features by using an attention mechanism to obtain the video attention audio feature specifically comprises:

$$\mathrm{VAAF} = [S_1^A, \ldots, S_{M_A}^A]\alpha$$

wherein VAAF is the video attention audio feature, $S_j^A$ (j=1, ..., $M_A$) is the feature of a <j>th audio segment, α is a video attention weight, and the calculation formula of each element in $\alpha = [\alpha_1, \ldots, \alpha_{M_A}]^T$ is as follows:

$$\alpha_j = \frac{e^{\langle L_V, s_j^A \rangle}}{\sum_{k=1}^{M_A} e^{\langle L_V, s_k^A \rangle}}, j = 1, \ldots, M_A$$

where $L_V$ is the video horizontal feature, $S_j^A$ (j=1, ..., $M_A$) is the feature of the <j>th audio segment, and e is a base of a natural logarithm.

Optionally, calculating the plurality of video segments by using the attention mechanism to obtain the audio attention video feature specifically comprises:

$$\mathrm{AAVF} = [S_1^V, \ldots, S_{M_V}^V]\beta$$

wherein AAVF is the audio attention video feature, $S_j^V$ (j=1, ..., $M_V$) is the feature of a <j>th video segment, β is an audio attention weight, and the calculation formula of each element in $\beta = [\beta_1, \ldots, \beta_{M_V}]$ is as follows:

$$\beta_j = \frac{e^{\langle L_A, s_j^V \rangle}}{\sum_{k=1}^{M_V} e^{\langle L_A, s_k^V \rangle}}, j = 1, \ldots, M_V$$

where $L_A$ is the audio horizontal feature, $S_j^V$ (j=1, ..., $M_V$) is the feature of the <j>th audio segment, and e is a base of a natural logarithm.

A third aspect of the embodiments of the application provides an electronic equipment, comprising a memory, a processor, and a computer program stored in the memory and operable on the processor, and characterized in that when the processor executes the computer program, the steps of the method according to the first aspect of the application are realized According to the automatic depression detection method provided by the application, the Fourier amplitude spectrum of the long-time audio file is extracted, the Fourier amplitude spectrum is obtained by fast Fourier assignment transform, the long-time Fourier amplitude spectrum is divided into the spectral segments with a fixed size, and the long-time video file is divided into the video segments with a fixed frame number; each spectral segment is input into the audio spatio-temporal attention network to extract the audio segment horizontal features, and each video segment is input into the video spatio-temporal attention network to extract the video segment horizontal features; the audio segment horizontal features and the video segment horizontal features are combined into the audio horizontal feature and the video horizontal feature respectively by means of the feature evolution pooling objective function; the plurality of audio segment horizontal features are calculated to obtain the video attention audio feature, and the plurality of video segment horizontal features are calculated to obtain the audio attention video feature; the audio horizontal feature, the video horizontal feature, the video attention audio feature and the audio attention video feature are spliced to form the multimodal spatio-temporal representation; and the multimodal spatio-temporal representation is input into support vector regression to predict the depression level of individuals. In this application, a short-time voice amplitude spectrum and the video segment horizontal features are extracted by using the spatio-temporal attention networks, which is beneficial to the extraction of distinctive features compared with the prior art. By using feature evolution pooling, information related to depression in all short-time audio-visual features is effectively included, so that short-time audio-video features and long-time audio-video features are combined. By using a multimodal attention feature fusion strategy, the features of both the audio mode and the video mode are fused, thereby enhancing the effect of depression detection and effectively improving the prediction accuracy of automatic depression detection.

BRIEF DESCRIPTION OF THE DRAWINGS

In order to explain the technical solution of the embodiments of this application more clearly, the drawings used in the description of the embodiments of this application will be briefly introduced below. Obviously, the drawings in the following description are only some embodiments of this application. For those of ordinary skill in the art, other drawings can be obtained according to these drawings without creative labor.

DETAILED DESCRIPTION OF THE EMBODIMENTS

The technical solution in the embodiments of this application will be described clearly and completely with reference to the drawings in the embodiments of this application. Obviously, the described embodiments are part of the embodiments of this application, not all of them. All other embodiments obtained by those of ordinary skill in the art based on the embodiments in this application without creative labor fall within the protection scope of this application.

Figure 1:
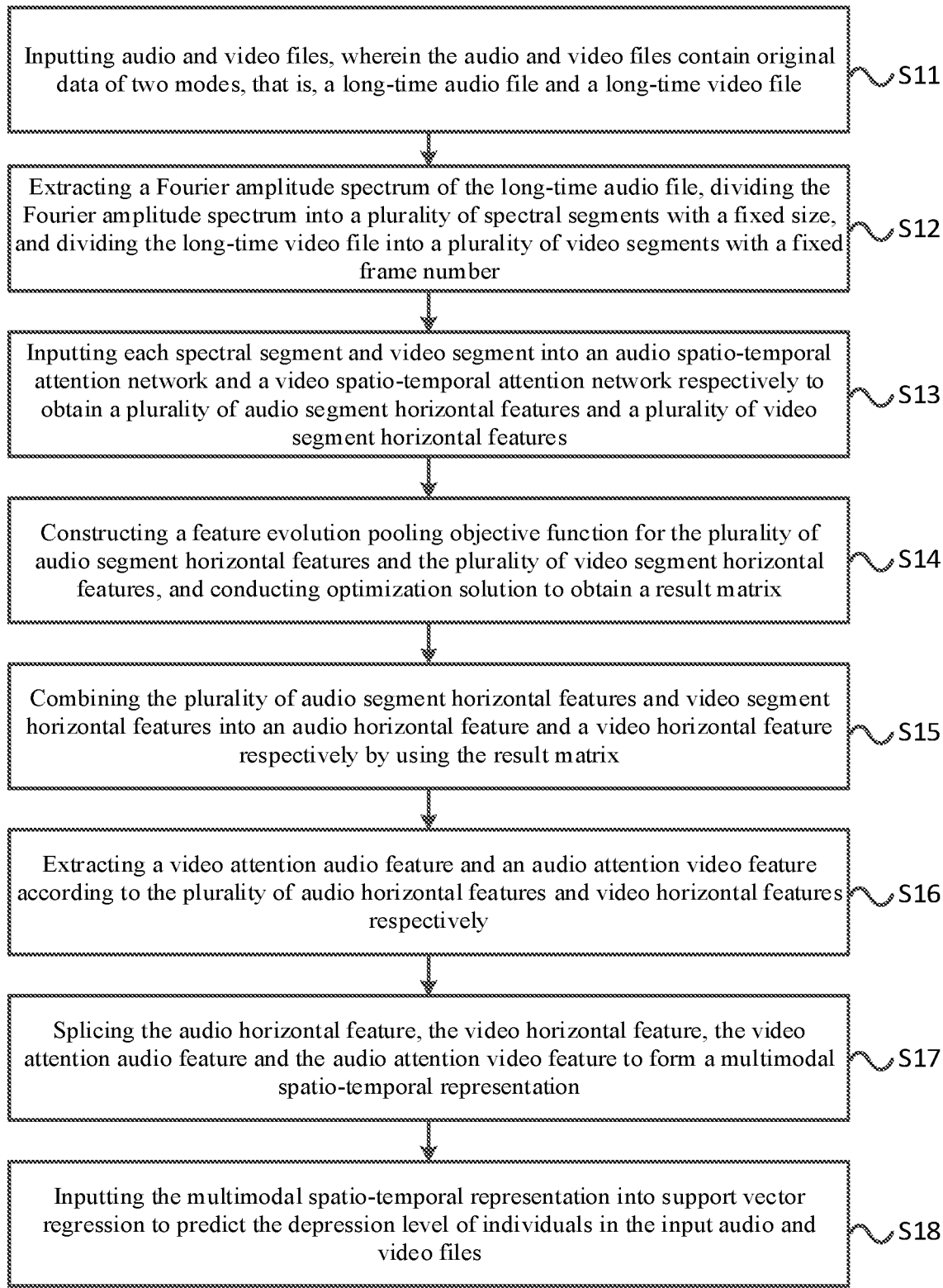
FIG. 1 is a flowchart of an automatic depression detection method according to an embodiment of the application.

Referring to FIG. 1, a flowchart of an automatic depression detection method according to an embodiment of the application is shown. As shown in FIG. 1, the method comprises the following steps:

S11: inputting audio and video files, wherein the audio and video files contain original data of two modes, that is, a long-time audio file and a long-time video file.

In this embodiment, in order to detect the depression level of an individual by detecting the voice, movements and expressions of the individual in the audio and video files, the audio and video files need to be input into a depression detection network, and the audio and video files need to contain the individual to be tested. The long-term audio file contains the original data of the audio mode, and the long-term video file contains the original data of the video mode.

S12: extracting a Fourier amplitude spectrum of the long-time audio file, dividing the Fourier amplitude spectrum into a plurality of spectral segments with a fixed size, and dividing the long-time video file into a plurality of video segments with a fixed frame number.

In this embodiment, the Fourier amplitude spectrum of the long-time audio file is obtained through Fourier transform of the audio information in the long-time audio file, and can reflect audio features. Dividing the Fourier amplitude spectrum into a plurality of spectral segments with a fixed size, and dividing the long-time video file into a plurality of video segments with a fixed frame number are beneficial to the extraction of audio and video features.

In this embodiment, extracting a Fourier amplitude spectrum of the long-time audio file, dividing the Fourier amplitude spectrum into a plurality of spectral segments with a fixed size, and dividing the long-time video file into a plurality of video segments with a fixed frame number specifically comprise the following steps:

S12-1: extracting a voice file from the long-time audio file with an original format of MP4, and saving the voice file in a way format to obtain a way file.

In this embodiment, in order to conduct Fourier transform on the audio file, a voice file needs to be extracted from the long-time audio file with an original format of MP4, and the voice file is saved in a way format to obtain a way file. Way files feature a real sound waveform, no compressed data and a large data size.

S12-2: processing the way file by means of fast Fourier transform to obtain a Fourier spectrum.

In this embodiment, fast Fourier transform is to conduct fast discrete Fourier transform computation on the audio file by using a computer, so that the Fourier spectrum of the audio file can be obtained efficiently and quickly.

For example, the fast Fourier transform of the audio file can be performed by using software such as MATLAB, which is not limited in this application.

S12-3: conducting amplitude calculation on the Fourier spectrum to obtain a Fourier amplitude spectrum.

In this embodiment, after the Fourier spectrum of the audio file is obtained, an amplitude in the Fourier spectrum is read to obtain the Fourier amplitude spectrum, which can show the amplitude of audio transformation at each moment, from which people's emotional changes can be analyzed.

For example, the Fourier amplitude spectrum can be obtained by using software such as MATLAB.

S12-4: dividing the Fourier amplitude spectrum by taking a first preset frame number as a window length and a second preset frame number as a frame shift to obtain the plurality of amplitude spectrum segments, wherein the label of the plurality of amplitude spectrum segments is the label corresponding to the way file.

In this embodiment, the Fourier amplitude spectrum can be divided in frames, and the Fourier amplitude spectrum can be divided by window sliding. The window length represents the maximum number of frames of amplitude spectrum content that can be displayed in a window, and the frame shift represents the distance that the window moves at one time calculated by the number of frames. The label of each amplitude spectrum segment is the label of the corresponding audio way file.

For example, the Fourier amplitude spectrum can be divided with 64 frames as the window length and 32 frames as the frame shift to obtain the amplitude spectrum segments.

S12-5: saving the amplitude spectrum segments in a mat format.

In this embodiment, the mat format is a data storage format of the MATLAB standard, and by storing the amplitude spectrum segments in the mat format, subsequent processing is facilitated.

S12-6: extracting all video frames in the long-time video file and normalizing all the video frames to a preset size to obtain a video frame sequence.

In this embodiment, extracting all the video frames in the long-term video file is to extract the image of each frame in the video file and normalize the images, that is, to perform normalization calculation on the images, so that the image of each frame becomes an image of a standard size, which makes processing easier.

For example, all the images can be normalized to a size of 128*128.

S12-7: dividing the video frame sequence by taking a third preset frame number as a window length and a fourth preset frame number as a frame shift to obtain video segments, wherein the label of the video segments is the label corresponding to the long-time video file.

In this embodiment, the video is also divided through window sliding, and the label of the video segments is the label corresponding to the long-time video file.

For example, the video frame sequence can be divided with 60 frames as the window length and 30 frames as the frame shift to obtain the video segments.

S13: inputting each spectral segment and video segment into an audio spatio-temporal attention network and a video spatio-temporal attention network respectively to obtain a plurality of audio segment horizontal features and a plurality of video segment horizontal features.

In this embodiment, inputting each spectral segment and video segment into an audio spatio-temporal attention network and a video spatio-temporal attention network respectively to obtain a plurality of audio segment horizontal features and a plurality of video segment horizontal features specifically comprises the following steps:

S13-1: inputting the marked spectral segments and video segments into the audio spatio-temporal attention network and the video spatio-temporal attention network respectively as training sets in advance for training, so as to obtain a trained audio spatio-temporal attention network and a trained video spatio-temporal attention network.

In this embodiment, the audio spatio-temporal attention network and the video spatio-temporal attention network can extract the audio segment horizontal features and the video segment horizontal features from the audio segments and the video segments. In a training set, individual depression levels in the spectral segments and the video segments can be marked, the marked spectral segments can be input into the audio spatio-temporal attention network, and the marked video segments can be input into the video spatio-temporal attention network. The audio spatio-temporal attention network and the video spatio-temporal attention network can constantly adjust their own parameters by learning the features in the training set, so as to obtain the trained audio spatio-temporal attention network and the trained video spatio-temporal attention network.

S13-2: inputting the plurality of spectral segments and the plurality of video segments into the trained audio spatio-temporal attention network and the trained video spatio-temporal attention network respectively to obtain the plurality of audio segment horizontal features and the plurality of video segment horizontal features.

In this embodiment, the trained audio spatio-temporal attention network may perform feature extraction on the input spectral segments to obtain the multiple audio segment horizontal features, and the trained video spatio-temporal attention network may perform feature extraction on the input video segments to obtain the multiple video segment horizontal features.

For example, the audio spatio-temporal attention network and the video spatio-temporal attention network may be networks such as CNN and RNN, which is not limited here.

S14: constructing a feature evolution pooling objective function for the plurality of audio segment horizontal features and the plurality of video segment horizontal features, and conducting optimization solution to obtain a result matrix.

In this embodiment, the feature evolution pooling objective function is constructed to fuse the multiple video segment features and the multiple audio segment features respectively. All the video segment features are input into the feature evolution pooling objective function for optimization, so as to obtain a result matrix for fusing the multiple video segment features. All the audio segment features are input into the feature evolution pooling objective function for optimization, so as to obtain a result matrix for fusing the multiple audio segment features.

In this embodiment, the feature evolution pooling objective function is:

$$G^* = \mathrm{argmin}_{G^T G = I_k} \Sigma_{i=1}^{D} \| G G^T d_i^T - d_i^T \|^2$$

wherein G is a known matrix, $G^T$ is a transposed matrix of the matrix G, $d_i^T$ is a transposition of an <I>th video segment horizontal feature or audio segment horizontal feature, D is the number of the audio segment horizontal features or the video segment horizontal features, $I_k$ indicates that the matrix G is a K-order matrix, $G^*$ is the result matrix, and argmin( ) indicates the value of a feature vector when the formula in the brackets reaches a minimum value.

In this embodiment, elements in the matrix G are known, the matrix G is optimized by calculation, and the final optimization result is $G^*$, that is, the result matrix.

S15: combining the plurality of audio segment horizontal features and video segment horizontal features into an audio horizontal feature and a video horizontal feature respectively by using the result matrix.

In this embodiment, after obtaining the result matrix, the plurality of audio segment horizontal features and video segment horizontal features can be fused through the result matrix to obtain the audio horizontal feature and the video horizontal feature, which specifically comprises:

S15-1: arranging the plurality of audio segment horizontal features and the plurality of video segment horizontal features into an audio matrix and a video matrix respectively in sequence.

In this embodiment, the plurality of audio segment horizontal features are arranged into a matrix according to the order of each audio segment horizontal feature in the Fourier amplitude spectrum, wherein each line is an eigenvector; and the plurality of video segment horizontal features are arranged into a matrix according to the order of the video segment corresponding to each video segment horizontal feature in the video, wherein each line is an eigenvector.

S15-2: multiplying the audio matrix and the video matrix by a first column of the result matrix respectively to obtain the audio horizontal feature and the video horizontal feature.

In this embodiment, by multiplying the audio matrix by a first column of the result matrix, the plurality of audio segment features are combined to obtain an overall feature, that is, the audio horizontal feature; and by multiplying the video matrix by the first column of the result matrix, the plurality of video segment features are combined to obtain an overall feature, that is, the video horizontal feature.

In this embodiment, after derivation and calculation, an eigenvector corresponding to a maximum eigenvalue of the product of the audio matrix or the video matrix and the transpose of the audio matrix or the video matrix is the same as an eigenvector corresponding to a maximum eigenvalue of a matrix obtained by multiplying the audio matrix or the video matrix with the first column of the result matrix.

Therefore, the audio horizontal feature and the video horizontal feature can also be expressed as:

calculating an eigenvalue and eigenvector of $S^T S$, where $S=[S_1, \ldots, S_M]$, and $S$ (j=1, … M) is an <j>th audio or video segment horizontal feature.

An eigenvector g* corresponding to a maximum eigenvalue of $S^T S$ is selected, and then Sg* is a result of combination.

S16: extracting a video attention audio feature and an audio attention video feature according to the plurality of audio horizontal features and video horizontal features respectively.

In this embodiment, the video attention audio feature is obtained by calculating the audio segment features to obtain the weight of the video segment features in the audio segment features, that is, the influence of the video segment features on the audio segment features. The same is true for the audio attention video feature, which represents the influence of the audio segment features on the video segment features. The audio segment feature and the video segment feature of the same frame correspond to each other.

In this embodiment, extracting a video attention audio feature and an audio attention video feature according to the plurality of audio horizontal features and video horizontal features respectively specifically comprises:

S16-1: calculating the plurality of audio segment horizontal features by using an attention mechanism to obtain the video attention audio feature.

In this embodiment, calculating the plurality of audio segment horizontal features by using an attention mechanism to obtain the video attention audio feature specifically comprises:

$$\text{VAAF}=[S_1^A, \ldots, S_{M_A}^A]\alpha$$

wherein VAAF is the video attention audio feature, $S_j^A$ (j=1, …, $M_A$) is the feature of a <j>th audio segment, α is a video attention weight, and the calculation formula of each element in $\alpha=[\alpha_1, \ldots, \alpha_{M_A}]^T$ is as follows:

$$\alpha_j = \frac{e^{\langle L_V, s_j^A \rangle}}{\sum_{k=1}^{M_A} e^{\langle L_V, s_k^A \rangle}}, j=1, \ldots, M_A$$

wherein $L_V$ is the video horizontal feature, $S_j^A$ (j=1, …, $M_A$) is the feature of the <j>th audio segment, and e is a base of a natural logarithm.

In this embodiment, the video attention audio feature is calculated by considering the influence of the video features on the audio features, and is the audio feature taking into account the influence of the video features.

S16-2: calculating the plurality of video segment horizontal features by using the attention mechanism to obtain the audio attention video feature.

In this embodiment, calculating the plurality of video segments by using the attention mechanism to obtain the audio attention video feature specifically comprises:

$$\text{AAVF}=[S_1^V, \ldots, S_{M_V}^V]\beta$$

wherein AAVF is the audio attention video feature, $S_j^V$ (j=1, …, $M_V$) is the feature of a <j>th video segment, β is an audio attention weight, and the calculation formula of each element in $\beta=[\beta_1, \ldots, \beta_{M_V}]^T$ is as follows:

$$\beta_j = \frac{e^{\langle L_A, s_j^V \rangle}}{\sum_{k=1}^{M_V} e^{\langle L_A, s_k^V \rangle}}, j=1, \ldots, M_V$$

where $L_A$ is the audio horizontal feature, $S_j^V$ (j=1, …, $M_V$) is the feature of the <j>th audio segment, and e is a base of a natural logarithm.

In this embodiment, the audio attention video feature is calculated by considering the influence of the audio features on the video features, and is the video feature taking into account the influence of the audio features.

S17: splicing the audio horizontal feature, the video horizontal feature, the video attention audio feature and the audio attention video feature to form a multimodal spatio-temporal representation.

In this embodiment, the audio horizontal feature, the video horizontal feature, the video attention audio feature and the audio attention video feature are spliced to form the multimodal spatio-temporal representation, which is to splice an audio horizontal eigenvector, a video horizontal eigenvector, a video attention audio eigenvector and an audio attention video eigenvector into a vector, which includes the features of both the video and audio modes and the features of their interaction.

For example, the audio horizontal feature $L_A$, the video horizontal feature $L_V$, the video attention audio feature VAAF and the audio attention video features AAVF are spliced to obtain a vector {$L_A$, $L_V$, VAAF, AAVF}, that is, the final multimodal spatio-temporal representation.

S18: inputting the multimodal spatio-temporal representation into support vector regression to predict the depression level of individuals in the input audio and video files.

In this embodiment, support vector regression is a classification model, which can score the depression level of individuals in the input audio and video files according to the received multimodal spatio-temporal representation. The support vector regression will score the depression level of individuals in the currently input audio and video files according to the features learned during previous training.

For example, the individual's depression level is measured by BDI-II scores. The BDI-II scores range from 0 to 63 (0-13 is no depression, 14-19 is mild depression, 20-28 is moderate depression, and 29-63 is severe depression), and the final prediction result is a real number between 0 and 63.

Figure 2:
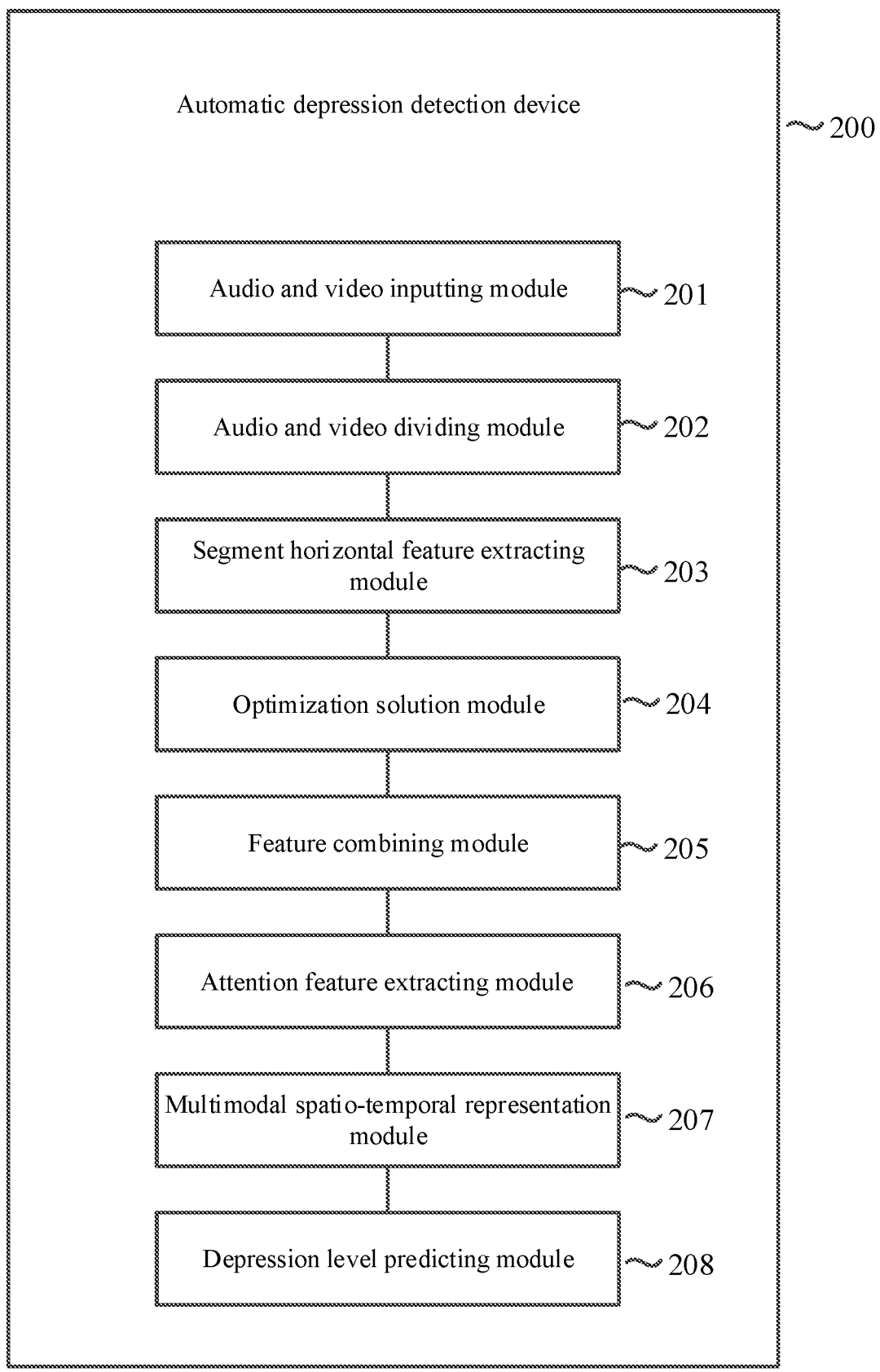
FIG. 2 is a diagram of an automatic depression detection device according to an embodiment of the application.

Based on the same inventive concept, an embodiment of the application provides an automatic depression detection device. Referring to FIG. 2, a diagram of an automatic depression detection device 200 according to an embodiment of the application is shown. As shown in FIG. 2, the device comprises:

an audio and video inputting module 201 for inputting audio and video files, wherein the audio and video files contain original data of two modes, that is, a long-time audio file and a long-time video file;

an audio and video dividing module 202 for extracting a Fourier amplitude spectrum of the long-time audio file, dividing the Fourier amplitude spectrum into a plurality of spectral segments with a fixed size, and dividing the long-time video file into a plurality of video segments with a fixed frame number;

a segment horizontal feature extracting module 203 for inputting each spectral segment and video segment into an audio spatio-temporal attention network and a video spatio-temporal attention network respectively to obtain a plurality of audio segment horizontal features and a plurality of video segment horizontal features;

an optimization solution module 204 for constructing a feature evolution pooling objective function for the plurality of audio segment horizontal features and the plurality of video segment horizontal features, and conducting optimization solution to obtain a result matrix;

a feature combining module 205 for combining the plurality of audio segment horizontal features and video segment horizontal features into an audio horizontal feature and a video horizontal feature respectively by using the result matrix;

an attention feature extracting module 206 for extracting a video attention audio feature and an audio attention video feature according to the plurality of audio horizontal features and video horizontal features respectively;

a multimodal spatio-temporal representation module 207 for splicing the audio horizontal feature, the video horizontal feature, the video attention audio feature and the audio attention video feature to form a multimodal spatio-temporal representation; and a depression level predicting module 208 for inputting the multimodal spatio-temporal representation into support vector regression to predict the depression level of individuals in the input audio and video files.

Optionally, the audio and video dividing module comprises:

a voice file extracting submodule for extracting a voice file from the long-time audio file with an original format of MP4, and saving the voice file in a way format to obtain a way file;

a fast Fourier transform submodule for processing the way file by means of fast Fourier transform to obtain a Fourier spectrum;

an amplitude extracting submodule for conducting amplitude calculation on the Fourier spectrum to obtain a Fourier amplitude spectrum;

an amplitude spectrum dividing submodule for dividing the Fourier amplitude spectrum by taking a first preset frame number as a window length and a second preset frame number as a frame shift to obtain the plurality of amplitude spectrum segments, wherein the label of the plurality of amplitude spectrum segments is the label corresponding to the way file;

an amplitude spectrum segment saving submodule for saving the amplitude spectrum segments in a mat format;

a video frame extracting submodule for extracting all video frames in the long-time video file and normalizing all the video frames to a preset size to obtain a video frame; and a video dividing submodule for dividing the video frame sequence by taking a third preset frame number as a window length and a fourth preset frame number as a frame shift to obtain video segments, wherein the label of the video segments is the label corresponding to the long-time video file.

Optionally, the segment horizontal feature extracting module comprises:

a network training submodule for inputting the marked spectral segments and video segments into the audio spatio-temporal attention network and the video spatio-temporal attention network respectively as training sets in advance for training, so as to obtain a trained audio spatio-temporal attention network and a trained video spatio-temporal attention network; and a segment horizontal feature extracting submodule for inputting the plurality of spectral segments and the plurality of video segments into the trained audio spatio-temporal attention network and the trained video spatio-temporal attention network respectively to obtain the plurality of audio segment horizontal features and the plurality of video segment horizontal features.

Optionally, in constructing a feature evolution pooling objective function for the plurality of audio segment horizontal features and the plurality of video segment horizontal features, and conducting optimization solution to obtain a result matrix, the feature evolution pooling objective function is:

$$G^* = \mathrm{argmin}_{G^T G = I_k} \sum_{i=1}^{D} \|GG^T d_i^T - d_i^T\|^2$$

wherein G is a known matrix, $G^T$ is a transposed matrix of the matrix G, $d_i^T$ is a transposition of an <I>th video segment horizontal feature or audio segment horizontal feature, D is the number of the audio segment horizontal features or the video segment horizontal features, $I_k$ indicates that the matrix G is a K-order matrix, G* is the result matrix, and argmin( ) indicates the value of an eigenvector when the formula in the brackets reaches a minimum value.

Optionally, the feature combining module comprises:

a feature arranging submodule for arranging the plurality of audio segment horizontal features and the plurality of video segment horizontal features into an audio matrix and a video matrix respectively in sequence; and a feature calculation submodule for multiplying the audio matrix and the video matrix by a first column of the result matrix respectively to obtain the audio horizontal feature and the video horizontal feature.

Optionally, the attention feature extracting module comprises:

a first attention feature extracting submodule for calculating the plurality of audio segment horizontal features by using an attention mechanism to obtain the video attention audio feature; and a second attention feature extracting submodule for calculating the plurality of video segment horizontal features by using the attention mechanism to obtain the audio attention video feature.

Optionally, calculating the plurality of audio segment horizontal features by using an attention mechanism to obtain the video attention audio feature specifically comprises:

$$\mathrm{VAAF} = [S_1^A, \ldots, S_{M_A}^A]\alpha$$

where VAAF is the video attention audio feature, $S_j^A$ (j=1, ..., $M_A$) is the feature of a <j>th audio segment, $\alpha$ is a video attention weight, and the calculation formula of each element in $\alpha = [\alpha_1, \ldots, \alpha_{M_A}]^T$ is as follows:

$$\alpha_j = \frac{e^{\langle L_V, s_j^A \rangle}}{\sum_{k=1}^{M_A} e^{\langle L_V, s_k^A \rangle}}, \quad j=1, \ldots, M_A$$

where $L_V$ is the video horizontal feature, $S_j^A$ (j=1, ..., $M_A$) is the feature of the <j>th audio segment, and e is a base of a natural logarithm.

Optionally, calculating the plurality of video segments by using the attention mechanism to obtain the audio attention video feature specifically comprises:

$$\mathrm{AAVF} = [S_1^V, \ldots, S_{M_V}^V]\beta$$

where AAVF is the audio attention video feature, $S_j^V$ (j=1, ..., $M_V$) is the feature of a <j>th video segment, $\beta$ is an audio attention weight, and the calculation formula of each element in $\beta=[\beta_1, \ldots, \beta_{M_V}]^T$ is as follows:

$$\beta_j = \frac{e^{(L_A, s_j^V)}}{\sum_{k=1}^{M_V} e^{(L_A, s_k^V)}}, j=1, \ldots, M_V$$

where $L_A$ is the audio horizontal feature, $S_j^V$ (j=1, ..., $M_V$) is the feature of the <j>th audio segment, and e is a base of a natural logarithm.

Based on the same inventive concept, another embodiment of the application provides electronic equipment, which comprises a memory, a processor, and a computer program stored in the memory and operable on the processor, and when the processor executes the computer program, the steps of the automatic depression detection method according to any embodiment described above are realized.

As the device embodiments are basically similar to the method embodiments, the description is relatively simple, and please refer to the description of the method embodiments for relevant information.

All the embodiments in this specification are described in a progressive way, and each embodiment focuses on the differences from other embodiments. The same and similar parts among the embodiments are referable to one another.

It should be understood by those skilled in the art that the embodiments of the application can be provided as methods, devices, or computer program products. Therefore, the embodiments of the application may take the form of an entirely hardware embodiment, an entirely software embodiment, or an embodiment combining software and hardware aspects. Furthermore, the embodiments of the application may take the form of a computer program product implemented on one or more computer usable storage media (including but not limited to magnetic disk memory, CD-ROM, optical memory, etc.) having computer usable program code embodied therein.

The embodiments of the application are described with reference to flowcharts and/or block diagrams of methods, terminal equipment (systems), and computer program products according to the embodiments of the application. It should be understood that each flow and/or block in the flowchart and/or block diagram, and combinations of flows and/or blocks in the flowchart and/or block diagram can be implemented by computer program instructions. These computer program instructions may be provided to a processor of a general purpose computer, special purpose computer, embedded processor, or other programmable data processing terminal equipment to produce a machine, such that the instructions executed by the processor of the computer or other programmable data processing terminal equipment produce a device for implementing the functions specified in one or more flows in the flowcharts and/or one or more blocks in the block diagrams.

These computer program instructions may also be stored in a computer-readable memory which can direct a computer or other programmable data processing terminal equipment to function in a particular manner, such that the instructions stored in the computer-readable memory produce an article of manufacture including an instruction device which implements the functions specified in one or more flows in the flowcharts and/or one or more blocks in the block diagrams.

These computer program instructions may also be loaded onto a computer or other programmable data processing terminal equipment such that a series of operational steps are performed on the computer or other programmable terminal equipment to produce a computer implemented process, such that the instructions executed on the computer or other programmable terminal equipment provide steps for implementing the functions specified in one or more flows in the flowcharts and/or one or more blocks in the block diagrams.

Although the preferred embodiments of the invention have been described, those skilled in the art can make additional changes and modifications to these embodiments once they know the basic inventive concepts. Therefore, the appended claims are intended to be interpreted as including the preferred embodiment and all changes and modifications that fall within the scope of the present application.

It should be also noted that herein, relational terms such as first and second are only used to distinguish one entity or operation from another entity or operation, and do not necessarily require or imply any such actual relationship or order between these entities or operations. The terms "comprise", "include" or any other variations thereof, are intended to cover a non-exclusive inclusion, such that a process, method, article, or terminal equipment which includes a list of elements does not include only those elements but also other elements not expressly listed or inherent to such process, method, article, or terminal equipment. Without further limitation, an element defined by the statement "includes a . . . " does not exclude the presence of another identical element in a process, method, article or terminal equipment that includes the element.

The automatic depression detection method and device, and the equipment provided by the application are described in detail above. Specific examples are applied herein to illustrate the principle and implementation of the application. The above embodiments are only used to help understand the method of the application and its core ideas. For those of ordinary skill in the air, according to the idea of this application, there will be some changes in the specific implementation and application scope. To sum up, the contents of this specification should not be understood as a limitation of this application.

The invention claimed is:
1. An automatic depression detection method, comprising the steps of:
inputting audio and video files, wherein the audio and video files contain original data of two modes comprising a long-time audio file and a long-time video file;
extracting a Fourier amplitude spectrum of the long-time audio file, dividing the Fourier amplitude spectrum into a plurality of spectral segments with a fixed size, and dividing the long-time video file into a plurality of video segments with a fixed frame number;
inputting each spectral segment and each video segment into an audio spatio-temporal attention network and a video spatio-temporal attention network respectively to obtain a plurality of audio segment horizontal features and a plurality of video segment horizontal features;
constructing a feature evolution pooling objective function for the plurality of audio segment horizontal features and the plurality of video segment horizontal features, and conducting an optimization solution to obtain a result matrix;
combining the plurality of audio segment horizontal features and the plurality of video segment horizontal features into an audio horizontal feature and a video horizontal feature respectively by using the result matrix;

extracting a video attention audio feature and an audio attention video feature according to the plurality of audio segment horizontal features and the plurality of video segment horizontal features respectively;

splicing the audio horizontal feature, the video horizontal feature, the video attention audio feature and the audio attention video feature to form a multimodal spatio-temporal representation; and inputting the multimodal spatio-temporal representation into a support vector regression to predict a depression level of individuals in the audio and video files.

2. The automatic depression detection method according to claim 1, wherein extracting the Fourier amplitude spectrum of the long-time audio file, dividing the Fourier amplitude spectrum into the plurality of spectral segments with the fixed size, and dividing the long-time video file into the plurality of video segments with the fixed frame number comprise:

extracting a voice file from the long-time audio file with an original format of MP4, and saving the voice file in a way format to obtain a wav file;

processing the way file by a fast Fourier transform to obtain a Fourier spectrum;

conducting an amplitude calculation on the Fourier spectrum to obtain the Fourier amplitude spectrum;

dividing the Fourier amplitude spectrum by taking a first preset frame number as a window length and a second preset frame number as a frame shift to obtain a plurality of amplitude spectrum segments, wherein a label of the plurality of amplitude spectrum segments is the label corresponding to the wav file;

saving the plurality of amplitude spectrum segments in a mat format;

extracting video frames in the long-time video file and normalizing the video frames to a preset size to obtain a video frame sequence; and dividing the video frame sequence by taking a third preset frame number as the window length and a fourth preset frame number as the frame shift to obtain the plurality of video segments, wherein a label of the plurality of video segments is the label corresponding to the long-time video file.

3. The automatic depression detection method according to claim 1, wherein inputting the plurality of spectral segments and the plurality of video segments into the audio spatio-temporal attention network and the video spatio-temporal attention network to obtain the plurality of audio segment horizontal features and the plurality of video segment horizontal features comprises:

inputting marked spectral segments and video segments into the audio spatio-temporal attention network and the video spatio-temporal attention network respectively as training sets in advance for a training to obtain a trained audio spatio-temporal attention network and a trained video spatio-temporal attention network; and inputting the plurality of spectral segments and the plurality of video segments into the trained audio spatio-temporal attention network and the trained video spatio-temporal attention network respectively to obtain the plurality of audio segment horizontal features and the plurality of video segment horizontal features.

4. The automatic depression detection method according to claim 1, wherein the feature evolution pooling objective function is as follows:

$$G^* = \mathrm{argmin}_{G^T G = I_k} \sum_{i=1}^{D} \|GG^T d_i^T - d_i^T\|^2;$$

wherein G is a known matrix, $G^T$ is a transposed matrix of the known matrix G, $d_i^T$ is a transposition of an $I^{th}$ video segment horizontal feature or an $I^{th}$ audio segment horizontal feature, D is a number of the plurality of audio segment horizontal features or the plurality of video segment horizontal features, $I_k$ indicating the known matrix G is a K-order matrix, $G^*$ is the result matrix, and argmin( ) indicates a value of an eigenvector when a formula in brackets reaches a minimum value.

5. The automatic depression detection method according to claim 1, wherein combining the plurality of audio segment horizontal features and the plurality of video segment horizontal features into the audio horizontal feature and the video horizontal feature respectively by using an optimization result of a feature combining evolution comprises:

arranging the plurality of audio segment horizontal features and the plurality of video segment horizontal features into an audio matrix and a video matrix respectively in sequence; and multiplying the audio matrix and the video matrix by a first column of the result matrix respectively to obtain the audio horizontal feature and the video horizontal feature.

6. The automatic depression detection method according to claim 1, wherein extracting the video attention audio feature and the audio attention video feature according to the plurality of audio segment horizontal features and the plurality of video segment horizontal features respectively comprises:

calculating the plurality of audio segment horizontal features by using an attention mechanism to obtain the video attention audio feature; and calculating the plurality of video segment horizontal features by using the attention mechanism to obtain the audio attention video feature.

7. The automatic depression detection method according to claim 6, wherein when calculating the plurality of audio segment horizontal features by using the attention mechanism to obtain the video attention audio feature, a calculation method is as follows:

$$\mathrm{VAAF} = [S_1^A, \ldots, S_{M_A}^A]\alpha;$$

wherein VAAF is the video attention audio feature, $S_j^A$ (j=1, ..., $M_A$) is a feature of a $j^{th}$ audio segment, $\alpha$ is a video attention weight, and a calculation formula of each element in $\alpha = [\alpha_1, \ldots, \alpha_{M_A}]^T$ is as follows:

$$\alpha_j = \frac{e^{\langle L_V, s_j^A \rangle}}{\sum_{k=1}^{M_A} e^{\langle L_V, s_k^A \rangle}}, j = 1, \ldots, M_A;$$

where $L_V$ is the video horizontal feature, $S_j^A$ (j=1, ..., $M_A$) is the feature of the $j^{th}$ audio segment, and e is a base of a natural logarithm.

8. The automatic depression detection method according to claim 6, wherein when calculating the plurality of video segment horizontal features by using the attention mechanism to obtain the audio attention video feature, a calculation method is as follows:

$$AAVF = [S_1^V, \ldots, S_{M_V}^V]\beta$$

wherein AAVF is the audio attention video feature, $S_j^V$ (j=1, ..., $M_V$) is a feature of a $j^{th}$ video segment, $\beta$ is an audio attention weight, and a calculation formula of each element in $\beta = [\beta_1, \ldots, \beta_{M_V}]^T$ is as follows:

$$\beta_j = \frac{e^{\langle L_A, s_j^V \rangle}}{\sum_{k=1}^{M_V} e^{\langle L_A, s_k^V \rangle}}, j = 1, \ldots, M_V;$$

where $L_A$ is the audio horizontal feature, $S_j^V$ (j=1, ..., $M_V$) is the feature of the $j^{th}$ audio segment, and e is a base of a natural logarithm.

9. An electronic equipment, comprising a non-transitory memory and a processor, wherein a computer program is stored in the memory and operable on the processor, when the processor executes the computer program, the steps of the automatic depression detection method according to claim 1 are realized.

* * * * *